(12) United States Patent
Loboda et al.

(10) Patent No.: US 10,139,332 B2
(45) Date of Patent: Nov. 27, 2018

(54) MASS CYTOMETRY APPARATUS AND METHODS

(71) Applicant: Fluidigm Canada Inc., Markham (CA)

(72) Inventors: Alexander V. Loboda, Thornhill (CA); Dmitry R. Bandura, Aurora (CA); Vladimir I. Baranov, Richmond Hill (CA)

(73) Assignee: Fluidigm Canada Inc., Markham (CA)

( * ) Notice: Subject to any disclaimer, the term of this patent is extended or adjusted under 35 U.S.C. 154(b) by 9 days.

(21) Appl. No.: 14/983,463

(22) Filed: Dec. 29, 2015

(65) Prior Publication Data

US 2016/0195466 A1    Jul. 7, 2016

Related U.S. Application Data

(60) Provisional application No. 62/097,397, filed on Dec. 29, 2014.

(51) Int. Cl.
| | | |
|---|---|---|
| *G01N 15/10* | (2006.01) | |
| *H01J 49/00* | (2006.01) | |
| *H01J 49/04* | (2006.01) | |
| *H01J 49/10* | (2006.01) | |
| *H01J 49/40* | (2006.01) | |
| *H01J 49/02* | (2006.01) | |
| *G01N 15/00* | (2006.01) | |

(52) U.S. Cl.
CPC ...... *G01N 15/1056* (2013.01); *H01J 49/0009* (2013.01); *H01J 49/025* (2013.01); *H01J 49/04* (2013.01); *H01J 49/105* (2013.01); *H01J 49/40* (2013.01); *G01N 2015/0065* (2013.01); *G01N 2015/1006* (2013.01)

(58) Field of Classification Search
CPC ...... H01J 49/0009; H01J 49/025; H01J 49/04; H01J 49/104; H01J 49/105; H01J 49/40; G01N 15/1056; G01N 2015/0065; G01N 2015/1006

See application file for complete search history.

(56) References Cited

U.S. PATENT DOCUMENTS

| | | | |
|---|---|---|---|
| 6,229,142 B1 | 5/2001 | Bateman et al. | |
| 7,479,630 B2 * | 1/2009 | Bandura | G01N 15/1404 250/288 |
| 8,536,519 B2 | 9/2013 | Holle | |
| 8,723,108 B1 | 5/2014 | Ugarov | |
| 2006/0024199 A1 | 2/2006 | Tao et al. | |

(Continued)

FOREIGN PATENT DOCUMENTS

| | | |
|---|---|---|
| WO | 2005093784 | 10/2005 |
| WO | 2006090138 | 8/2006 |

(Continued)

OTHER PUBLICATIONS

Giesen et al., Highly multiplexed imaging of tumor tissues with subcellular resolution by mass cytometry, Nature Methods, vol. 11, 2014, pp. 417-422.

Stephan et al., Correction of dead time effects in time-of-flight mass spectrometry, J. Vac. Sci. Technol. vol. 12, 1994, p. 405-410.

Tanner et al., An introduction to mass cytometry: fundamentals and applications, Cancer Immunology, Immunotherapy, vol. 62, Issue 5, May 2013, pp. 955-965.

(Continued)

*Primary Examiner* — David E Smith
(74) *Attorney, Agent, or Firm* — Kilpatrick Townsend & Stockton LLP

(57) ABSTRACT

The inventors have improved mass cytometer to facilitate its use for the analysis of particles.

17 Claims, 6 Drawing Sheets

(56) References Cited

U.S. PATENT DOCUMENTS

| | | | |
|---|---|---|---|
| 2009/0057547 A1 | 3/2009 | Green et al. | |
| 2009/0108191 A1* | 4/2009 | Yefchak | H01J 49/0009 |
| | | | 250/252.1 |
| 2011/0024615 A1 | 2/2011 | Tanner et al. | |
| 2015/0212132 A1* | 7/2015 | Green | G01R 29/26 |
| | | | 250/281 |

FOREIGN PATENT DOCUMENTS

| | | |
|---|---|---|
| WO | 2011098834 | 8/2011 |
| WO | 2014091243 | 6/2014 |

OTHER PUBLICATIONS

Tyler, The accuracy and precision of the advanced Poisson dead-time correction and its importance for multivariate analysis of high mass resolution ToF-SIMS data, Surface and Interface Analysis, vol. 46, Issue 9, Sep. 2014, pp. 581-590.

Bandura et al., Mass Cytometry: Technique for Real Time Single Cell Multitarget Immunoassay Based on Inductively Coupled Plasma Time-of-Flight Mass Spectrometry, Anal. Chem. vol. 81, No. 16, Aug. 15, 2009, pp. 6813-6822.

Bendall et al., Deep Profilers Guide to Cytometry, Trends Immunol, vol. 33(7), Available online at: http://www.ncbi.nlm.nih.gov/pmc/articles/PMC3383392, Jul. 2012, pp. 323-332.

Bodenmiller et al., Multiplexed mass cytometry profiling of cellular states perturbed by small-molecule regulator, Nat Biotechnol, vol. 30(9), Sep. 2012, pp. 858-867.

Brückner et al., DNA Quantification via ICP-MS Using Lanthanide-Labeled Probes and Ligation-Mediated Amplification, Anal. Chem. vol. 86(1), Nov. 12, 2013, pp. 585-591.

Gao et al., Direct labeling microRNA with an electrocatalytic moiety and its application in ultrasensitive microRNA assays, Biosensor Bioelectronics vol. 22(6), Jan. 15, 2007, pp. 933-940.

Giesen et al., Multiplexed Immunohistochemical Detection of Tumor Markers in Breast Cancer Tissue Using Laser Ablation Inductively Coupled Plasma Mass Spectrometry, Anal. Chem., vol. 83 (21), Sep. 18, 2011, pp. 8177-8183.

Hutchinson et al., Imaging and spatial distribution of beta-amyloid peptide and metal ions in Alzheimer's plaques by laser ablation-inductively coupled plasma-mass spectrometry, Analytical Biochemistry, vol. 346(2), Nov. 15, 2005, pp. 225-233.

International Application No. PCT/US2015/067961, International Search Report and Written Opinion dated May 31, 2016, 12 pages.

International Application No. PCT/US2015/067961, Invitation to Pay Additional Fees and Partial Search Report dated Mar. 15, 2016, 2 pages.

Seuma et al., Combination of immunohistochemistry and laser ablation ICP mass spectrometry for imaging of cancer biomarkers, Proteomics, vol. 8, Issue 18 No. 18, Aug. 19, 2008, pp. 3775-3784.

Tyler et al., Dead-time correction for time-of-flight secondary-ion mass spectral images: a critical issue in multivariate image analysis, Surface and Interface Analysis, vol. 45, Issue 1, Jan. 2013, pp. 475-478.

* cited by examiner

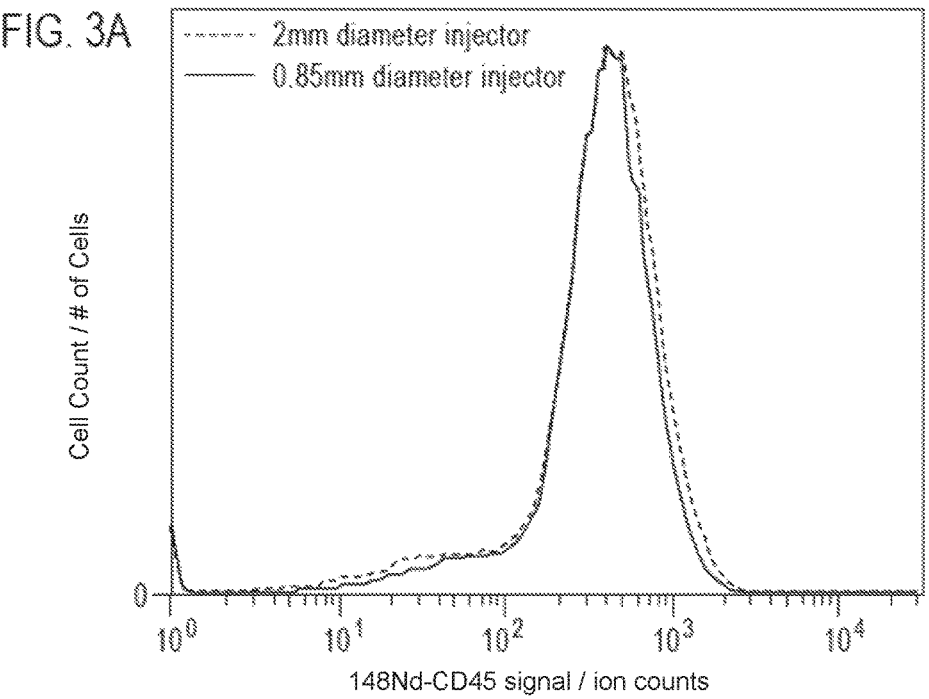
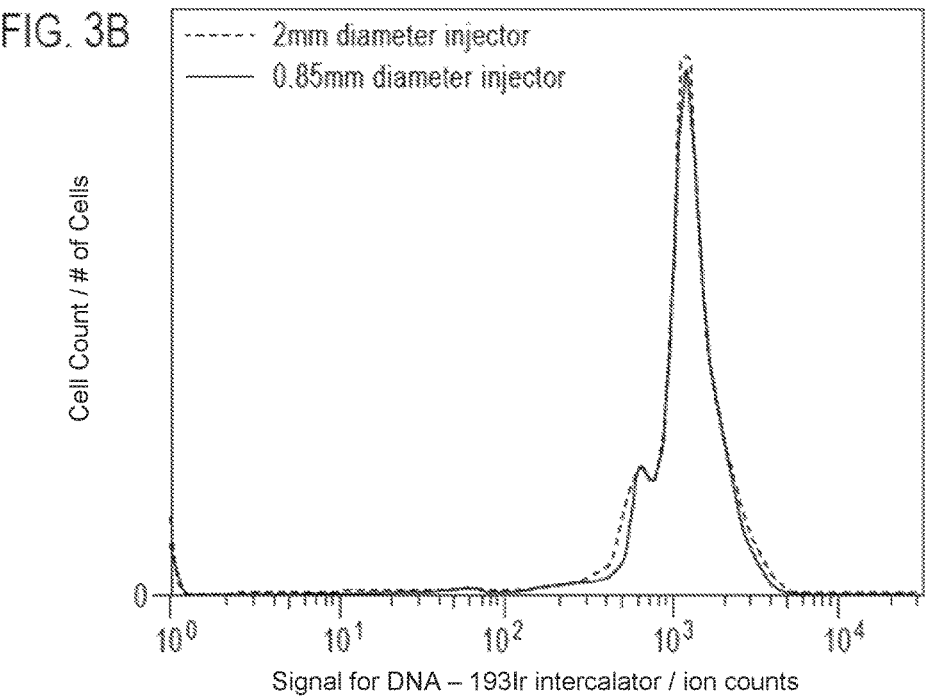

MASS CYTOMETRY APPARATUS AND METHODS

CROSS-REFERENCE TO RELATED APPLICATIONS

This application claims the benefit of and priority to U.S. Provisional Patent Application No. 62/097,397 filed Dec. 29, 2014, the contents of which are incorporated herein in its entirety.

FIELD

The present invention relates to the analysis of particles using mass cytometry.

BACKGROUND

The ability to analyse single particles, for example single cells or single beads, is useful because it allows the properties of each member of a population to have its properties determined separately. This therefore provides a greater insight than a single measurement that is simply the average of the properties of each member of the population.

A fluorescence based flow cytometry (e.g., fluorescence activated cell sorter (FACS) or the like) can measure the properties of cells or particles by scanning them as they pass through a laser beam. By labelling the cells or particles with fluorescent dyes specific to cell components, for example, receptors on the cell surface and DNA of the cell nucleus, the amount of labelled component can be detected as fluorescence when the particle or cell traverses the excitation beam. Since the amount of fluorescence emitted is proportional to the amount of fluorescent probe bound to the cell/antigen, antibodies conjugated to fluorochromes are routinely used as reagents to measure the antigen both qualitatively and quantitatively on and in the cell. Deficiencies of this approach are related to limitations and difficulties of cell staining methods and spectral overlap of fluorochromes. In other words, the detected emission of fluorochromes is not all at a specific wavelength, which means that when multiple labels are used, some of the detected emitted light can be mistakenly assigned to an incorrect label. This therefore limits the discriminatory power of the technique.

A technique, which overcomes this problem is mass cytometry [1,2]. It is analogous to flow cytometry in that a label is specifically attached to the material being analysed. The label is specifically targeted to an antigen on the cell or particle, using a specific binding partner, for example an antibody. The label is different between flow cytometry and mass cytometry. In mass cytometry, the one or more detectable labels are atoms of a known specific mass, typically transition metals, such as the rare earth metals. Accordingly, when the detectable labelling atoms are detected by the MS, it can be inferred that the target of the specific binding partner is present in the sample being analysed.

SUMMARY

In an aspect, mass cytometers are provided, comprising: (a) a sampler (e.g., a sample introduction system); (b) an ion source which is an inductively coupled plasma (ICP) from an ICP torch, wherein the ICP torch comprises an injector that at the end of the injector proximal to the plasma has an internal diameter of less than 2 mm and more than 250 µm; and (c) a mass spectrometer.

In another aspect, mass cytometers are provided, comprising: (a) a sampler (e.g., a sample introduction system); (b) an ion source of a mass spectrometer; (c) the mass spectrometer having a mass analyser; d) an ion detector of the mass spectrometer; and (e) an ion deflector of the mass spectrometer positioned between the ICP torch and the ion detector of the mass spectrometer, operable to control the entry into the ion detector of the mass spectrometer of ions exiting the ICP.

In another aspect, mass cytometers are provided, comprising: (a) a sampler (e.g., a sample introduction system); (b) an ion source; (c) a mass analyser of a mass spectrometer comprising a detector (e.g., ion detector) and/or an amplifier; and (d) an analog-digital correlator programmed to control the voltage of the amplifier and/or the voltage applied to the ion detector of the mass spectrometer to control the gain of the detector.

In another aspect, mass cytometers are provided, comprising: (a) a sampler (e.g., a sample introduction system); (b) an ion source; (c) a mass spectrometer having a mass analyser; and (d) a mass-assignment corrector that compares the peak shape of the signal from one or more mass channels on the mass analyser of the MS to an expected shape, and reassigns ions detected in the M±1 channels to the M channel, for each analysed channel.

In another aspect, mass cytometers are provided, comprising: (a) a sampler (e.g., a sample introduction system); (b) an ion source; (c) a mass spectrometer comprising a mass analyser and/or a detector (e.g., ion detector); and (d) a dead-time corrector that compensates for detector dead-time.

In another aspect, methods for performing mass cytometry are provided, comprising: (i) detecting a quantity of a detectable atom using a mass cytometer comprising a sampler (e.g., a sample introduction system), an ion source, and mass spectrometer having a mass analyser, the mass spectrometer comprising a detector (e.g., ion detector) and an analog-digital converter, and recording the digital signal from the analog-digital converter in the mass spectrometer as a first digital output; (ii) detecting the same quantity of the same detectable atom, and recording the digital signal from the analog-digital converter in the mass spectrometer as a second digital output; (iii) comparing the first digital output to the second digital output; (iv) modulating the voltage on the ion detector and/or the amplifier of the mass spectrometer based on the difference or ratio between the first digital output and the second digital output, so that the ratio of the first digital output and the second digital output is sustained at a constant, prescribed value; and (v) analysing a sample in the mass cytometer. In some embodiment the first digital output is the number of ions counted for the detectable analyte, while the second digital output is the analog signal generated by the same ions of the detectable analytes. In some embodiments the voltage on the ion detector is modulated or adjusted so that the analog signal or the ion counting signal, or both, are kept at a constant, prescribed value.

In some embodiments, a mass cytometer may be provided that includes a sample introduction system; a mass spectrometer comprising an ion source; a pressurized gas source operatively coupled with the ion source; and a pressure system. The sample introduction system may include an intake tube configured to be disposed within a sample fluid. The pressure system may be configured to apply a pressure to the sample fluid to force the sample fluid into the intake tube. The pressure system may be operatively coupled with the same gas source that is operatively coupled with the ion source.

In some aspects, a mass cytometer may be provided that includes an ion source; an ion detector and a mass analyser; an ion path between the ion source and the ion detector; and an ion deflector positioned along the ion path between the ion source and the ion detector. The ion deflector may be configured to selectively deflect ions to control entry of ions into the ion detector. In some embodiments, the ion deflector may be powered by DC voltages which will be selectively switched in order to modulate the ion path from the ion detector.

Optionally, the ion deflector, when activated, directs ions into the ion detector. In some embodiments, the ion detector may not receive ions from the ion source along the ion path when the deflector is deactivated.

In some embodiments, the ion detector receives ions from the ion source along the ion path when the ion deflector is deactivated. The ion deflector, when activated, may not direct ions into the ion detector in some embodiments.

The mass cytometer may further include a controller configured to at least one of activate or deactivate the ion deflector in response to a rate of change of counts of ions hitting the ion detector. The rate of change of counts of ions hitting the ion detector may be associated with a leading edge of a signal peak. The rate of change of counts of ions hitting the ion detector may be indicative that a subsequent portion of ions will exceed a detection limit associated with the ion detector.

In some embodiments, the mass cytometer may further include a control module operatively coupled with the ion detector and the ion deflector. The control module may be configured to modulate the ion deflector based on feedback from the ion detector of at least one of the number and rate of ions hitting the detector.

The mass analyser may be a TOF mass analyser configured to push ions toward the ion detector. The ion deflector may be controlled in response to an ion count in an initial push of ions toward the ion detector. The ion deflector may be modulated when the ion count in the initial push is within a predetermined threshold of the detection limit of the ion detector. The predetermined threshold may be 10% or less of the upper detection limit of the ion detector.

Optionally, the mass cytometer may include a controller configured to at least one of activate or deactivate the ion deflector in response to a count of ions detected by the ion detector.

In further aspects, a mass cytometer may include an ion source; an ion detector including secondary plates; a mass analyser; an analog-digital correlator coupled with the ion detector. The analog-digital correlator may be configured to vary a voltage applied across secondary plates of the detector in response to a detector signal associated with a standard.

The analog-digital correlator may be configured to compare the detector signal associated with the standard to an expected digital readout. In some embodiments, the analog-digital correlator varies the voltage applied across secondary plates of the detector such that the detector signal associated with the standard would match the expected digital readout. The expected digital read-out may comprise the ratio of an analog read-out and of the pulse-counting read-out for the ion signal of the ions of the same mass.

Optionally, the analog-digital correlator may be configured to vary the voltage applied across the detector prior to the introduction of each sample. In further embodiments, the analog-digital correlator may be configured to vary the voltage applied across the detector during a sample run.

In further aspects of the present disclosure, a mass cytometer may be provided that includes a sampler; an ion source; a mass analyser; and a mass-assignment corrector that compares the peak shape of a signal from a mass channel from the mass analyser to an expected peak shape associated with the mass channel, and reassigns ions detected in the M±1 channels to the M channel based on the comparison, for each analysed channel.

In still further aspects of the present disclosure, a mass cytometer may be provided that includes an ion source; an ion detector; a mass analyser; and a dead-time corrector coupled with the ion detector. The dead-time corrector may be configured to compare a first signal associated with a first ion mass to a threshold, and, when the first signal exceeds the threshold, the dead-time corrector may be configured to apply a correction to a subsequent signal associated with a second ion mass that is greater than the first ion mass to compensate for a temporary depression of an analog signal from the ion detector caused by the first signal associated with the first ion mass.

A peak height of the first signal may be compared to the threshold. Optionally, a peak area of the first signal may be compared to the threshold.

The dead-time corrector may be configured to apply the correction to the subsequent signal by multiplying the subsequent signal by a multiplier. The multiplier may be a function of an amount in which the first signal exceeds the threshold. The first ion mass may be n, and the second ion mass may be n+1. Optionally, the first ion mass may be n, and the second ion mass may be n+2, n+3, or n+4.

BRIEF DESCRIPTION OF THE DRAWINGS

The drawings described below are for illustration purposes only and are not intended to limit the scope of this disclosure.

FIG. 3A and FIG. 3B shows distributions of signals from CD45-Nd148 labelled antibody and Ir193 labelled DNA intercalator induced by stained cells KG1A when injected via exemplary 0.85 mm and 2 mm diameter ICP torch injectors.

DETAILED DESCRIPTION

A mass cytometer typically includes three core components. The first is a sampler (e.g., a sample introduction system) for taking a sample (usually comprising particles) to be analysed into the mass cytometer. After it has been taken into the mass cytometer, before the atoms in the sample (including the detectable labelling atoms) can be detected by a mass spectrometer (MS), the sample must be ionised. Accordingly, the mass cytometer also comprises an ion source that vaporises the sample to its constituent atoms and then ionises the atoms to enable their separation and/or detection by the mass analyser of the MS based on mass/charge ratio. Thus the sample is taken into the system, is ionised by the ion source, and the ions of the sample are passed into the mass analyser, and then detected in the ion detector of the MS. Although the MS of the mass cytometer can detect many ions, most of these will be ions of the atoms that naturally make up the particles. However, by labelling the particles with atoms not present in the particles under normal conditions (for example transition metal atoms, such as rare earth metals), specific characteristics of the particle can be determined. In common with flow cytometry, the detectable labels can be attached to specific markers on or in the particles (e.g., cells), inter alia through the use of antibodies or nucleic acids targeting molecules on or in the particles. In order to detect the ionised label, an MS is used. Usually, the particles are introduced into the ion source one at a time, thereby ensuring that the resulting atoms detected by the MS can be assigned to a specific particle, in turn enabling individual characterisation, particle-by-particle. Sometimes, however, multiple particles are deliberately ionised and detected at the same time.

Figure 1:
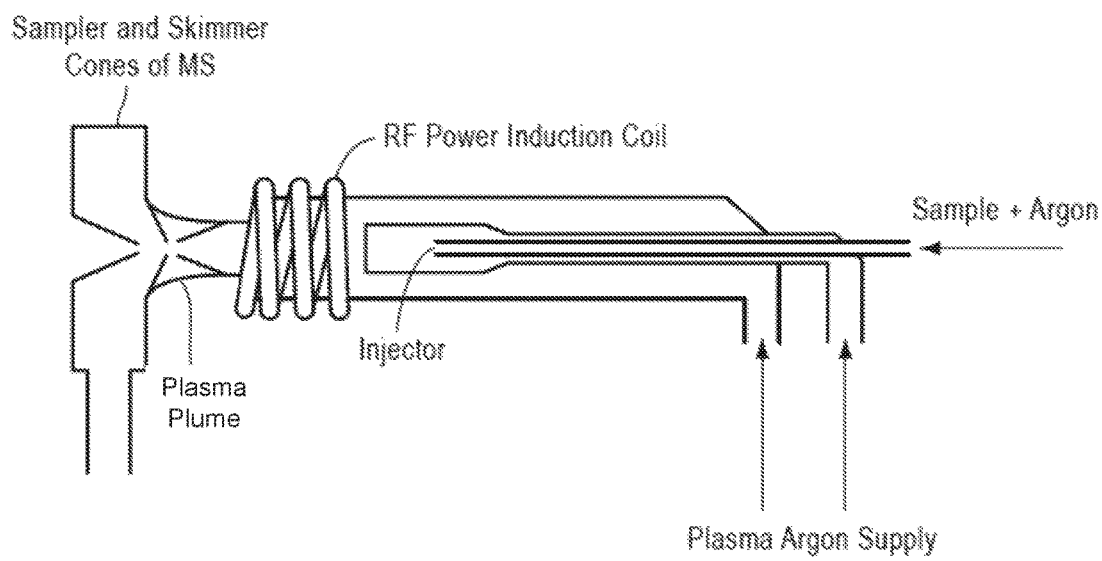
FIG. 1 shows a schematic diagram of an exemplary ICP torch and the plasma-vacuum interface of the mass cytometer.

Typical mass cytometers use an inductively coupled plasma (ICP) as the ion source before the ionised material is then introduced into the mass analyser of the MS and then detected. The ICP is maintained in an ICP torch, as illustrated in FIG. 1 and discussed in more detail below. Mass spectrometers can resolve ions one atomic mass unit apart, with minimal interference between the mass channels. A time of flight (TOF) detector is typically used. The present invention provides advances over previous mass cytometers, such as that disclosed in reference 3.

Sometimes, the sampler or sample introduction system does not process liquid samples, but is a part of a laser ablation apparatus. In this situation, a laser ablates material from a sample, and the aerosolised ablated material is carried to the ion source by gas flow. Ionisation and detection of the ionised labelling atoms then proceeds as in normal mass cytometry. A recent publication on this technique is reference 4.

Sample Introduction

Previous mass cytometers have used sample loops to hold the sample of cells or particles before their introduction into the ICP of the system. For example, the commercially available CyTOF®2 (Fluidigm Canada, Inc.) has two 0.5 mLloops, which as a result of the configuration of the valve that they are controlled by, operate in different manners. One is a first in, first out loop, and the other is a last in, first out loop. In usual operation, the user of the system manually injects the sample into the loop. When the user must inject the sample into the system this carries a risk that different people performing what is meant to be the same injection, or even the same person performing repeats of the same injection, will not have a consistent technique and so introduce variation into the results generated from the analysis.

Some mass cytometers of the invention comprise an autosampler that automates the process of taking sample into the mass cytometer system for subsequent analysis. An autosampler is a robotic component that takes accurate volumes (which may be user-defined) of sample into the system, from one or more vessels outside of the system. The autosampler therefore enables multiple samples to be subjected to mass cytometry without supervision of the system by a user, and with greater accuracy and repeatability than manual sample introduction.

The autosampler includes an aspirator, which is a tube-like component that dips into the liquid sample to allow the sample to be sucked into the system. The aspirator component may be made of plastic or metal. The aspirator is in fluid connection with the sample aerosolizer, for example, a pneumatic nebulizer, which is supplying the sample in the aerosol form to the ICP torch, and therefore sample can be transferred from the autosampler to the ICP torch for vaporisation, ionisation and then analysis of its ions in the MS. The autosampler may also comprise a pump that moves the sample into and through the autosampler. The position of the aspirator is controllable in the x, y and z axes, for example by being placed on a motor-controlled arm. X and y are perpendicular movements in the horizontal plane (and so are used to move the aspirator from the location of one sample to another sample at a different location e.g., different wells in a multi-well plate), and z is vertical movement (which is used to dip the aspirator in and out of samples).

The user can define which samples are to be analysed and in which order, and the autosampler can aspirate sample from each in turn, following analysis of the preceding sample by the mass cytometer. In some instances the autosampler is programmed so as to commence aspiration of the (n+1)th sample before detection of the nth sample has been completed, for example to compensate for the time taken in the manipulation and/or movement of the sample before it reaches the ICP and so make the sampling process more efficient. The autosampler can also be used with single samples.

In some embodiments, a sample introduction system may include an intake tube configured to be disposed within the sample fluid. The introduction system may be a pneumatic system that includes a pressure system. The pressure system may be configured to modulate a pressure applied to the sample (e.g., through the introduction or removal of gas pressure or the like). When the sample is ready to be introduced into the mass cytometry system, the pressure system may increase the pressure in the head space above the sample which will force the sample into the intake tube of the sample introduction system and into the mass cytometer system. In some embodiments, the gas pressure may be provided by a gas source. The gas source may be the same gas source that delivers gas to the ICP source.

In some embodiments, an autosampler may include an intake tube and the pneumatic system that includes the pressure system, so that when a sample from the autosampler tray or a separate autosampler vial is ready to be introduced into the mass cytometry system, the pressure system may increase the pressure in the head space above the sample which will force the sample into the intake tube of the sample introduction system and into the mass cytometer system. In some embodiments, the gas pressure may be provided by a gas source. The gas source may be the same gas source that delivers gas to the ICP source.

Inductively Coupled Plasma Torch

In mass cytometry, an inductively coupled plasma is used to ionise the material to be analysed before it is passed to the mass analyser of the MS for analysis. It is a plasma source in which the energy is supplied by electric currents produced by electromagnetic induction. FIG. 1 shows a schematic diagram of an exemplary ICP torch. The inductively coupled plasma is sustained in a torch that consists of three concentric tubes, the innermost tube being known as the injector.

The induction coil that provides the electromagnetic energy that maintains the plasma is located around the output end of the torch. The alternating electromagnetic field reverses polarity many millions of times per second. Argon gas is supplied between the two outermost concentric tubes. Free electrons are introduced through an electrical discharge and are then accelerated in the alternating electromagnetic field whereupon they collide with the argon atoms and ionise them. At steady state, the plasma consists of mostly of argon atoms with a small fraction of free electrons and argon ions.

The ICP can be retained in the torch because the flow of gas between the two outermost tubes keeps the plasma away from the walls of the torch. A second flow of argon introduced between the injector (the central tube) and the intermediate tube keeps the plasma clear of the injector. A third flow of gas is introduced into the injector in the centre of the torch. Samples to be analysed are introduced through the injector into the plasma.

Prior art mass cytometry systems (e.g., CyTOF®2; Fluidigm Canada, Inc.) use an injector with an internal diameter of 2 mm. This internal diameter or larger was previously favoured to ensure that the injector did not block when particles, in particular biological material such as cells, were passed through it to be ionised in the ICP.

Figure 2:
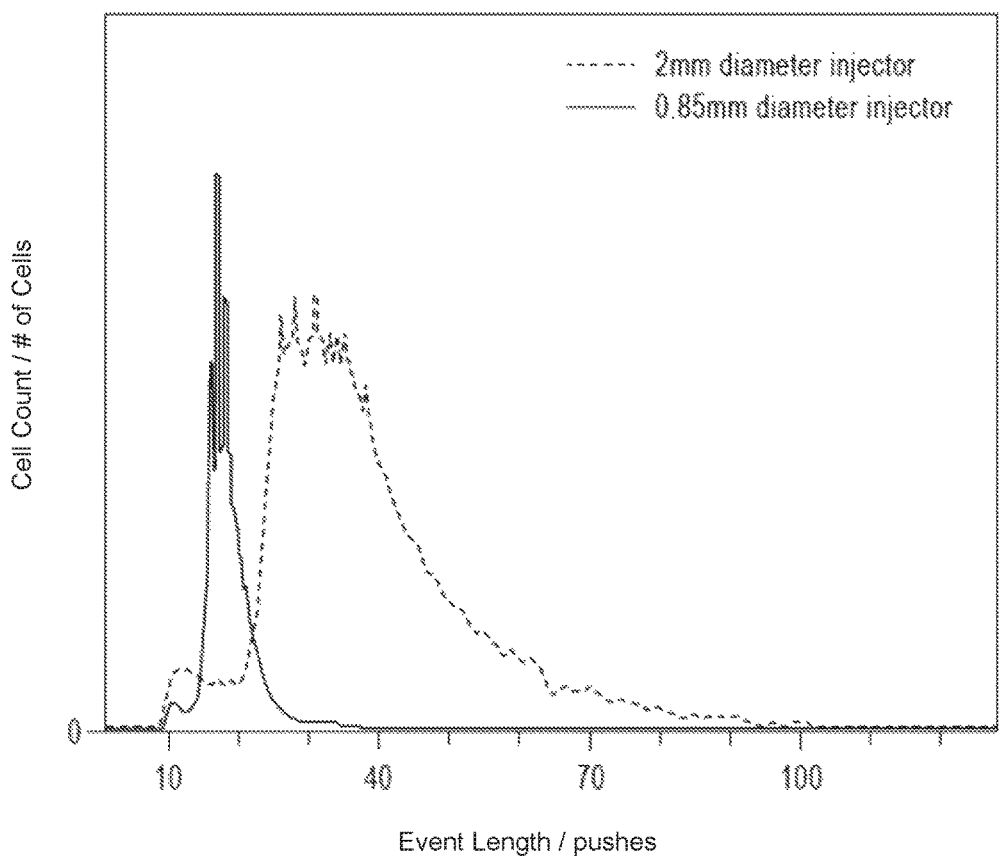
FIG. 2 shows histogram (or a distribution) of the length (e.g., duration) of the detection events induced by cells following injection by exemplary 0.85 mm and 2 mm internal diameter ICP torch injectors.
Figure 4A:
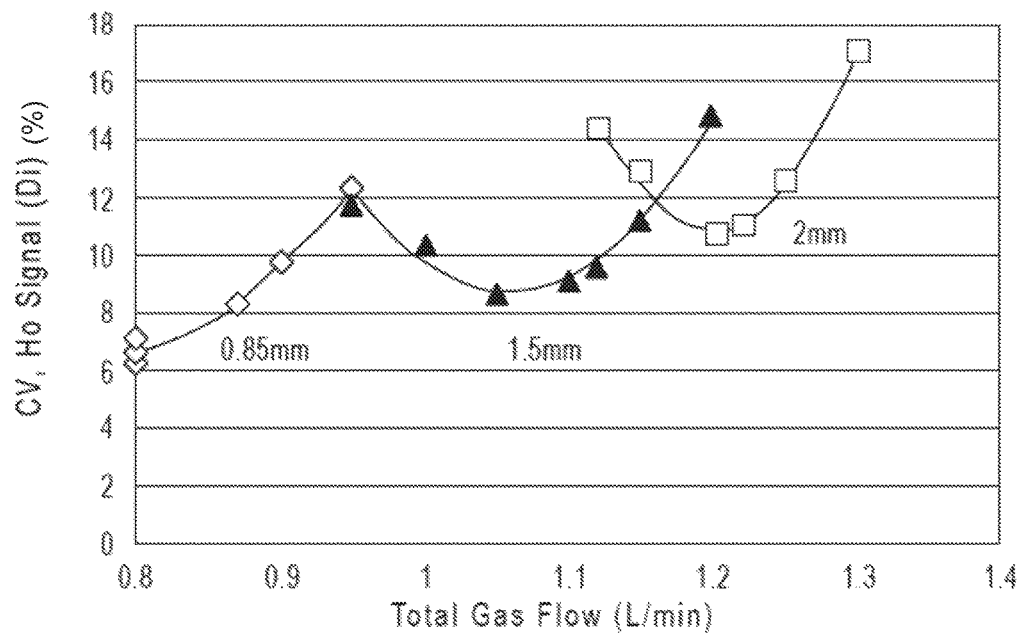
FIGS. 4A, 4B, 4C, and 4D shows a characterisation of 0.85 mm, 1.5 mm and 2 mm ICP torch injectors.
Figure 4B:
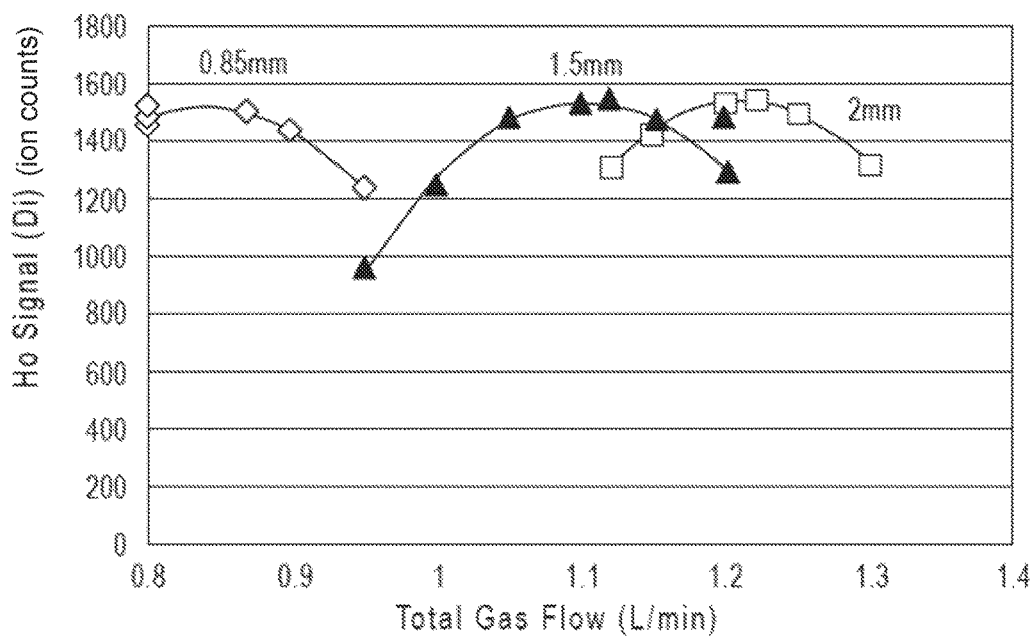

In contrast, in some embodiments described herein, the mass cytometer of the present invention comprises an injector with an internal diameter of less than 2 mm and more than 250 µm for introducing material from the sample into the plasma. The diameter of the injector refers to the internal diameter of the injector at the end proximal to the plasma. Extending away from the plasma, the injector may be of a different diameter, for example a wider diameter, wherein the difference in diameter is achieved through a stepped increase in diameter or because the injector is tapered along its length. In particular embodiments, the internal diameter of the injector is between 1.75 mm and 250 µm, such as between 1.5 mm and 300 µm in diameter, between 1.25 mm and 300 µm in diameter, between 1 mm and 300 µm in diameter, between 900 µm and 300 µm in diameter, between 900 µm and 400 µm in diameter, for example around 850 µm in diameter. The use of an injector with an internal diameter less than 2 mm provides significant advantages over injectors with a larger diameter, such as is used in the previous CyTOF®2 system even with cellular samples. One advantage of this feature is that the transience of the signal detected in the MS when a particle is introduced into the plasma is reduced with a narrower injector. Accordingly, the time taken to analyse a particle from its introduction into the ICP for ionisation until the detection of the resulting ions in the MS is reduced. This decrease in time taken to analyse a particle enables more particles to be detected in any given time period (see FIGS. 2 and 5). There is no difference in total signal between sample introduction into the plasma using an injector of an internal diameter of 0.85 mm versus 2 mm, as shown in FIGS. 3A and 3B, where the histograms of the signal distribution resulting from analysis of particles comprising a known amount of a detectible atom using injectors of these diameters can be seen to overlap. Also, an injector with a smaller internal diameter results in the more accurate introduction of particles into the centre of the inductively coupled plasma, where turbulence in the plasma gas flows can cause significant deflection of particles to the periphery, increasing time of their transience through the plasma and into the sampler cone. Further, use of an injector with an internal diameter less than 2 mm helps to reduce "doublet" events where two particles or cells are introduced into the plasma at the same time (event being used as a term to generally describe the passage of material generating a detectable signal into the ICP and subsequent detection by MS). An improved property in the analysis of particles is set out in the upper left-hand chart in FIG. 4B, which shows a lower coefficient of variance of the signal generated by monodispersed beads embedded with Holmium for smaller diameter injectors when a gas flow optimised to each diameter of injector is used (i.e. the CV at the bottom of the trough for the 0.85 mm injector is lower than that for the 1.5 mm injector, which in turn is lower than that for the 2 mm injector).

The injector is typically made of quartz, but can be made of alumina (such as sapphire) or platinum. The injector usually should be made from material that does not comprise atoms which will interfere with the detection of signals from the sample (e.g., if the sample matrix is hydrofluoric acid then it can corrode the injector as the sample is injected into the plasma, meaning a signal from the injector would be detected by the MS). Zirconium is present in some forms of quartz, meaning that it is possible that zirconium could leach from the injector and would be detected by the MS if a corrosive material is passed through the injector. Accordingly, in some embodiments, the injector is made of quartz, which contains no zirconium or has a very low zirconium content. These injectors have utility in situations where zirconium is used as a detectable labelling atom for labelling the sample.

ICP torches (Agilent, Varian, Nu Instruments, Spectro, Leeman Labs, PerkinElmer, Thermo Fisher etc.) and injectors (for example from Elemental Scientific and Meinhard) are available.

Ion Deflector

Mass spectrometers detect ions when they hit a surface of their detector. The collision of an ion with the detector causes the release of electrons from the detector surface. These electrons are multiplied as they pass through the detector (the first released electron knocks out further electrons in the detector), these electrons then hit secondary plates which further amplify or multiply the number of electrons. The number of electrons hitting the anode of the detector generates a current. The number of electrons hitting the anode can be controlled by altering the voltage applied to the secondary plates. The current is an analog signal that can then be converted into a count of the ions hitting the detector by an analog-digital converter. When the detector is operating in its linear range, the current can be directly correlated to the number of ions. The quantity of ions that can be detected at once has a limit (which can be expressed as the number of ions detectable per second). Above this point, the number of electrons released by ions hitting the detector is no longer correlated to the number of ions. This therefore places an upper limit on the quantitative capabilities of the detector.

When ions hit the detector, its surface becomes damaged by contamination. Over time, this irreversible contamination damage results in fewer electrons being released by the detector surface when an ion hits the detector, with the ultimate result that the detector needs replacing. This is termed "detector aging", and is a well-known phenomenon in MS.

Detector life can therefore be lengthened by avoiding the introduction of overloading quantities of ions into the MS. As noted above, when the total number of ions hitting the MS detector exceeds the upper limit of detection, the signal is not as informative as when the number of ions is below the upper limit because it is no longer quantitative. It is therefore desirable to avoid exceeding the upper limit of detection as it results in accelerated detector aging without generating useful data.

Analysis of particles, such as beads or cells, by mass spectrometry or mass cytometry involves a particular set of challenges not found in normal mass spectrometry. In particular, typical ICP-MS techniques involve introducing a low and constant level of material into the detector (as the material introduced into the ICP has been previously nebulised to very small particles), which should not approach the upper detection limit or cause accelerated aging of the detector. On the other hand, mass cytometry-based techniques analyse a relatively large amount of material in a very short time window in the MS: e.g., the ions from a cell-sized particle, which is much larger than the small particles typically analysed in ICP-MS. In effect, it is a deliberate almost overloading of the detector with each particle analysed. In between the particle analysis events the signal is at baseline (a signal that is close to zero because no ions from labelling atoms are deliberately being entering into the MS from the ICP; some ions can be detected because the plasma sustaining gases and their impurities are ionised, e.g. Ar, Xe, if they are not removed from an ion beam by an ion pre-treatment device or the like).

Thus in mass cytometry versus typical ICP-MS, there is an elevated risk of accelerated detector aging, because the ions from particles labelled with a large number of detectable atoms, or the introduction of the ions from multiple particles in a single event, can exceed the upper limit of detection and damage the detector without providing useful data. Such overloads are particularly common when analysing biological samples, because of the propensity of some cell types to aggregate. Accordingly, rather than the total number of ions expected, for example, from one cell per event, a number of cells can sometimes be introduced with the corresponding number of labelling atoms which can damage the detector.

To address these issues, in some embodiments the mass cytometer comprises an ion deflector positioned between the ICP torch and ion detector of the mass spectrometer, operable to control the entry of ions into the ion detector of the MS. When the ion deflector is on, the ions received from the ICP are deflected (i.e. the path of the ions is changed and so the ions do not reach the detector), but when the deflector is off the ions are not deflected and reach the detector. How the ion deflector is deployed will depend on the arrangement of the ICP and MS components of the mass cytometer. If the portal through which the ions enter the mass analyser and ion detector of the MS is not directly in line with the path of ions exiting the ICP, then by default the appropriately arranged ion deflector will be on, in order to direct ions from the ICP into the mass analyser and ion detector of the MS. When an event resulting from the ionisation of one or more particles considered likely to overload the ion detector of the MS is detected (see below), the ion deflector is switched off, so that the rest of the ionised material from the event is not deflected into the detector of the MS and can instead simply hit an internal surface of the system, thereby preserving the life of the MS detector. The ion deflector is returned to its original state after the ions from the damaging event have been prevented from entering the detector of the MS, thereby allowing the ions from subsequent particles to enter the detector of the MS and be detected.

Alternatively, in arrangements where (under normal operating conditions) there is no change in the direction of the ions emerging from the ICP before they enter the analyser or detector of the MS the ion deflector will be off, and the ions from the ICP will pass through it to be analysed in the MS. To prevent damage when a potential overload of the detector is detected, in this configuration the ion deflector is turned on, and so diverts ions so that they do not enter the detector in order to prevent damage to the detector.

The ions entering the MS from ionisation of a particle do not enter the MS all at the same time, but instead enter as a peak with a frequency that follows a probability distribution curve about a maximum frequency: from baseline, at first a small number of ions enters the MS and are detected, and then the frequency of ions increases to a maximum before the number decreases again and trails off to baseline. An event likely to damage the detector can be identified because instead of a slow increase in the frequency of ions at the leading edge of the peak, there is a very quick increase in counts of ions hitting the detector.

Figure 4C:
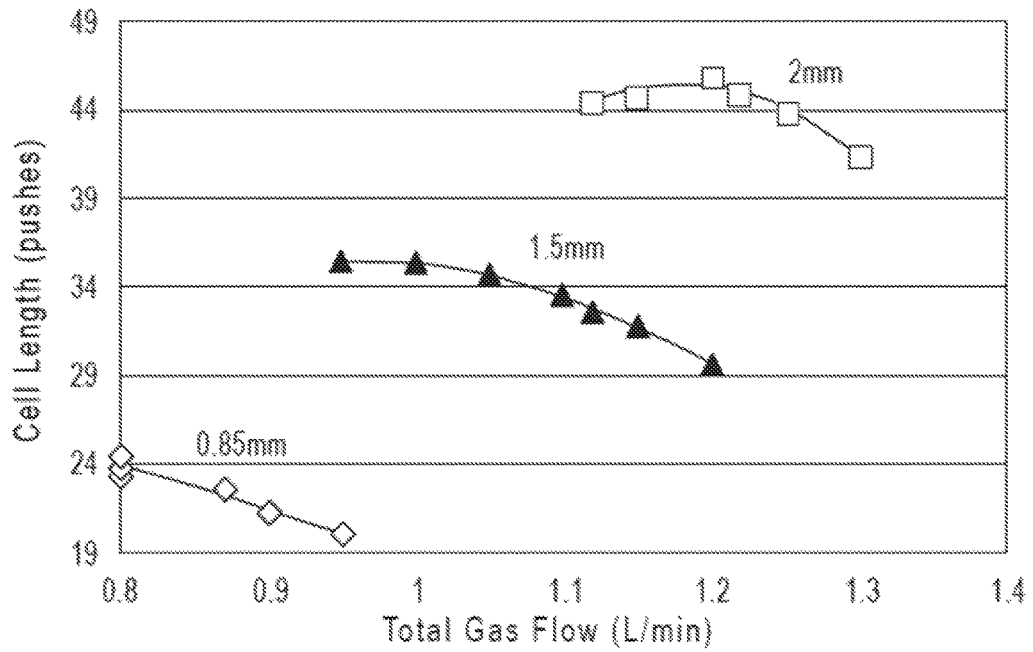

The flow of ions hitting the detector of a TOF MS is not continual during the analysis of the ions of a particle. The TOF comprises a pulser, which releases the ions periodically into the flight chamber of the TOF MS in pulsed groups (by generating a "push" of ions). By releasing the ions all at the known same time, the time of flight mass determination is enabled. The time between the releases of pulses of ions for time of flight mass determination is known as TOF cycle time or an extraction or push of the TOF MS. The push or cycle time is in the order of microseconds. Typical transience time of a particle through the ICP is several hundred of microseconds. The signal from one or more particles ionised by the ICP therefore covers a number of cycles (or "pushes") (e.g., the bottom left hand corner of FIG. 4C, which measures transience in terms of the number of pushes). The push pulse may be approximately 2.5 microsecond in some embodiments, and may be repeated every cycle time (of 13 microseconds in some embodiments). Thus, one can say that the event takes approximately 20 pushes to be detected.

Accordingly, when the ion count reading jumps from the baseline to a very high count within one push (i.e. the first portion of the ions from a particular particle) then it can be predicted that the main body of ions resulting from ionisation of the particle will be even greater, and so exceed the upper detection limit. It is at this point that an ion deflector can be operated to ensure that the damaging bulk of the ions are directed away from the detector (by being activated or deactivated, depending on the arrangement of the system, as discussed above).

In one particular embodiment, the MS used is a TOF MS with a push or cycle time of 50 μs or quicker, such as a scan or cycle time of 25 μs or quicker, 20 μs or quicker, 15 μs or quicker, 13 μs or quicker, 10 μs or quicker, or 5 μs or quicker. In one particular embodiment the scan or cycle time is 13 μs or quicker.

In some embodiments, the mass cytometer comprises a control module that operates (by activating or deactivating it, as appropriate) the ion deflector positioned between the ICP torch and the ion detector of the mass spectrometer, to prevent ions exiting the ICP from entering the detector of the MS. The control module runs a program that depends on feedback from the detector of the number of ions hitting the detector. In some embodiments, the MS is TOF MS, and whether there is a damaging quantity of ions is the determined by the ion count in the first push of ions as a particle is detected in the MS. In some embodiments, the damaging quantity of ions in the first push of ions is set at 10% or less of the upper detection limit of the detector, such as 5% or less, 1% or less, 0.5% or less, 0.1% or less, 0.05% or less or 0.01% or less. The absolute value of ion count determined to be damaging will therefore depend on the detector employed in the MS. For example, the deflector may be activated or deactivated by the programmed controller when, in the first push of ions from the particle, the TOF MS detects a total ion count of 500 or more, for example, 1000 ions or more, for example, 2000 ions or more, 3000 ions or more, 5000 ions or more, 10000 ions or more or 20000 ions or more. In some embodiments the deflector is activated or deactivated by 10000 ions or more. An alternative criterion for activating or deactivating the deflector takes the detection capacity of the detector in ions per second and divides this by the push time, to identify the upper limit of detection per push. For example, if the detector can detect 100 million ions per second, and the scan time is 20 µs, then that equates to a total of 2000 ions per scan. Setting a limit to activate or deactivate the detector less than 2000 ions per scan, regardless of whether it is the first push or any other push of the ion peak, therefore would protect the detector from being overloaded. In some embodiments, an electrostatic ion deflection may be activated through the feedback loop from the detector, or preamplifier, or digitizer.

Suitable ion deflectors based on quadrupoles are available in the art (e.g, from Colutron Research Corporation (now Beam Imaging Solutions) and Dreebit GmbH).

In another embodiment, a deflector is provided which comprises one pair or plurality of pairs of electrodes, in the shape of plates or thin wires, and positioned in the path of the ion packets as they pass through the time-of-flight analyser after being pushed out by the pulser. In such embodiment, the controller may be programmed in such a manner, that the deflector is activated for a period of time which is shorter than the duration of one cycle, in each cycle, so that the deflection of ions is done in a mass-specific manner. Mass-specific deflection may be based on the magnitude of the signal in the first push. The mass-specific deflection can be utilized if the deflector is at a particular focal point in the TOF section. In another embodiment, such deflector is activated for the time which is the same or longer than the cycle time, so that ions of all masses are prevented from entering the detector.

Calibration of Detector to Improve Inter and Intra-Sample Consistency

As noted above, a particular problem in performing mass cytometry on particles (e.g., cells) or other techniques which involve passing large concentrated quantities of ions into the MS in a short period of time (such as ions from plumes of ablated material in LA-ICP-MS), is that the detector ages during use. When this occurs, even though the same number of ions will be hitting the detector, the current or voltage produced by the detector is lower as fewer electrons are released in the aged detector by the one or more collisions between secondary electrons and the surfaces of the detector. When passed through an analog-digital converter, this means that the detected ion count will be reported to be lower, purely through aging of the detector even when the same number of ions is hitting the detector.

This detector aging can be controlled for by using a standard that comprises a known quantity of a detectable atom. The standard may be in the form of particles (such as polystyrene beads doped with a detectable atom), or may be xenon isotopes which are present as impurities in the argon used to form the plasma of the ICP (if a broadly consistent level of xenon is provided due to the purification procedures used to obtain the argon, for example). When xenon is used as the calibrator, the level of xenon ions can be detected before a sample is analysed and then this value is used as the known standard for any subsequent calibration. As the expected digital readout of the standard is then known, the voltage applied across the secondary plates of the detector (which act as a multiplier of the electron current generated from collisions of ions with the first surface of the detector or an amplifier of the signal from the detector) can be varied subsequently so that the analog signal (i.e. the number of electrons resulting from an ion collision, as determined by the resulting voltage) when converted by the analog-digital converter results in a digital signal that matches the expected digital signal, to ensure consistency between different experiments. Effectively, the gain of the detector or amplifier is kept constant despite the surfaces of the detector being aged (methods for the automatic control of detector gain or amplification in TOF MS are known [5]). The calibration can be performed at the start of each sample run (e.g., detecting xenon, or where standard beads are used, the beads are introduced into the mass cytometer at the start of every sample that is run), for example within the first two seconds of the experiment. When larger samples are run through the mass cytometer, as enabled by the use of an autosampler as discussed above, then rather than performing this calibration at the start of the sample only, it is possible to detect the standard (e.g., scan for xenon or run the standard beads) periodically during the sample to control for aging of the detector during the sample run.

Accordingly, the invention provides a mass cytometer comprising an analog-digital correlator that controls the voltage of the detector of the mass spectrometer. In some embodiments, the correlator is a control module (such as a computer or a programmed chip) configured to adjust the voltage of the detector of the mass spectrometer detector so as to alter the analog output from the detector such that, when converted to a digital signal, the digital signal corresponds to an expected digital output, for example using the method set out below. The expected digital output can be the signal expected from the plasma xenon or running doped particles (e.g., polystyrene beads) containing a known quantity of one or more detectable atoms through the mass cytometer.

In some embodiments, the expected digital output can be the difference or ratio of analog intensity and pulse counting signals expected from the standard measured. For example, when xenon concentration in argon gas is used as a standard, the xenon concentration may vary too much from tank to tank. Accordingly, in some embodiments, the analog signal associated with the xenon by itself may be insufficient to act as an expected digital output. In such situations, the analog signal of the standard may be measured along with the ion count which is associated with the analog intensity. The ratio of the ion count to the analog intensity associated with the ion count provides information on the degree by which the analog intensity is attributable, on average, to a single ion count (detector gain) and may be used as an expected output for calibration purposes (e.g., an expected ratio or predetermined ratio or expected detector gain). This ratio is associated with the ion detector gain. When the ion detector ages, the analog intensity will decrease relative to the associated ion count and as such, during calibration, the calculated ratio between analog intensity and ion count will differ from the expected ratio (when the detector is new). Thereafter, voltage may be applied across the detector to compensate for the decreased analog intensity such that the ratio between the analog intensity and the ion count returns toward the expected ratio. Put in another way, the applied voltage to the detector helps maintain the detector gain constant or otherwise substantially constant throughout the life of the detector and, in some embodiments, during a sample run. Accordingly, in some embodiments, the difference or ratio of analog intensity to ion count may be used as a predetermined standard. This implementation may be more practical when the standard (e.g., xenon concentration in argon gas) varies day to day or from sample to sample.

The invention also provides a method for performing mass cytometry comprising:
(i) detecting a quantity of a detectable atom using a mass cytometer comprising a sampler, ion source, and mass spectrometer, the mass spectrometer comprising a detector and an analog-digital converter, and recording the digital signal from the analog-digital converter in the mass spectrometer as a first digital output;

(ii) detecting the same quantity of the same detectable atom, and recording the digital signal from the analog-digital converter in the mass spectrometer as a second digital output;

(iii) comparing the first digital output to the second digital output;

(iv) modulating the voltage on the detector of the mass spectrometer based on the difference or ratio between the first digital output and the second digital output, so that the analog signal produced by the detector following conversion by the analog-digital converter would result in the same digital signal as the first digital output (which may be the same difference or ratio between the first digital output and the second digital output in some embodiments); and (v) analysing a sample in the mass cytometer.

In some embodiments, the method further comprises repeating steps (ii)-(iv) during the performance of step (v).

In some embodiments, the mass cytometer of the invention comprises an analog-digital correlator for performing steps (iii) and (iv), so that the modulation of voltage on the detector or amplifier is automated.

Mass-Assignment Corrector

The inventors have observed a number of behaviours in the signals detected by the MS in the mass cytometer. The vast majority of ionisation events generate $M^+$ ions, where a single electron has been knocked out of the atom. Because of the mode of operation of the TOF MS there is sometimes some bleeding (or cross-talk) of the ions of one mass (M) into the channels for neighbouring masses (M±1), in particular where a large number of ions of mass M are entering the detector (i.e. ion counts which are high, but not so high that an ion deflector positioned between the ICP and MS would prevent them from entering the MS, if the mass cytometer were to comprise such an ion deflector). As the arrival time of each $M^+$ ion at the detector follows a probability distribution about a mean (which is known for each M), when the number of ions at mass $M^+$ is high, then some will arrive at times that would normally be associated with the $M-1^+$ or $M+1^+$ ions. However, as each ion has a known distribution curve upon entering the TOF MS, based on the peak in the mass M channel it is possible to determine, the overlap of ions of mass M into the M±1 channels (by comparison to the known peak shape). Accordingly, it is therefore possible to correct the readings for the M−1, M and M+1 channels to appropriately assign all of the mass M ions. The invention therefore provides a mass cytometer comprising a mass-assignment corrector that compares the peak shape of the signal from one or more mass channels on the MS to an expected shape, and reassigns ions detected in the M±1 channels to the M channel, for each analysed channel. In some embodiments, the mass-assignment corrector is a control module (such as a computer or a programmed chip), wherein the control module is programmed to compare the peak shape of the signal from one or more mass channels on the MS to the expected shape, and to reassign ions detected in the M±1 channels to the M channel, for each analysed channel. The inventors determined that such corrections have particular use in correcting mass cytometry data due to the nature of the large particulate samples analysed by the technique. Programs and methods for improving the quality of data by de-convoluting the data from TOF MS are discussed in references 6, 7 and 8.

Dead-Time Corrector

As noted above, signals in the MS are detected on the basis of collisions between ions and the detector, and the release of electrons from the surfaces of the detector hit by the ions and secondary electrons. The inventors observed that when a high count of ions is detected by the MS resulting in the release of a large number of electrons, the detector of the MS can become temporarily fatigued, with the result that the analog signal output from the detector is temporarily depressed for one or more of the subsequent ions. In other words, a particularly high count or group of ions of a particle size (i.e., a particular mass) may cause a lot of electrons to be released from the detector surface and secondary multiplier in the process of detecting the group of ions of that particle size, meaning that fewer electrons are available to be released when the group of ions of subsequent/consecutive particles sizes (i.e., masses similar to the prior mass of the ions detected) hits the detector in the same cycle, until the electrons in the detector surface and secondary amplifier are replenished.

Based on a characterisation of the behaviour of the detector, the inventors have determined that it is possible to compensate for this dead-time phenomenon in a mass cytometer. A first step is to analyse the ion peak in the analog signal resulting from the detection of the nth particle size by the detector. The magnitude of the peak may be determined by the height of the peak, by the area of the peak, or by a combination of peak height and peak area.

The magnitude of the peak is then compared to see if it exceeds a predetermined threshold. If the magnitude is below this threshold, then no correction is necessary. If the magnitude is above the threshold, then correction of the digital signal associated with at least one subsequent particle size (i.e., mass) will be performed (at least the (n+1)th particle size (i.e. mass), but possibly further particle sizes, such as (n+2)th, (n+3)th, (n+4)th etc.) to compensate for the temporary depression of the analog signal from these particle sizes resulting from the fatiguing of the detector caused by the nth particle size (mass). The greater the magnitude of the peak associated with the nth particle size (i.e. mass), the more peaks associated with subsequent particle sizes will need to be corrected and the magnitude of correction will need to be greater. The dead-time corrector can be programmed to: (i) record an ion peak resulting from detection of a first particle size; (ii) compare the magnitude of the ion peak associated with the first particle size to a defined threshold, and (iii) if the magnitude of the ion peak associated with the first particle size exceeds the defined threshold, the digital signal associated with one or more subsequent particle sizes is multiplied by the corrector, dependent upon the extent that the threshold is exceeded by the ion peak associated with the first particle size. Methods for correcting such phenomena are discussed in references 9, 10, 11, 12 and 13, and these methods can be applied by the dead-time corrector to mass cytometry data, as described herein.

Accordingly, in some embodiments, the dead-time corrector is a control module (such as a computer or a programmed chip), wherein the dead-time corrector is programmed to record an ion peak resulting from detection of a first particle and if the magnitude of the ion peak of the first particle exceeds a defined threshold, the control module multiplies the digital signal of one or more subsequent particles dependent upon the extent that the threshold is exceeded by the ion peak of the first particle.

Mass Spectrometer

The time taken to analyse the ionised material will depend on the type of mass analyser which is used for detection of ions. For example, instruments which use Faraday cups are generally too slow for analysing rapid signals. Overall, the desired analysis speed (and thus the frequency with which particles can be based) and degree of multiplexing will dictate the type(s) of mass analyser which should be used (or, conversely, the choice of mass analyser will determine the speed and multiplexing which can be achieved).

Mass spectrometry instruments that detect ions at only one mass-to-charge ratio (m/Q, commonly referred to as m/z in MS) at a time, for example using a mass filter type of mass analyser and a single ion detector or point ion detector, will give poor results mass cytometry using multiple labels. Firstly, the time taken to switch between mass-to-charge ratios limits the speed at which multiple signals can be determined, and secondly, if ions are at low abundance then signals can be missed when the instrument is focused on other mass-to-charge ratios. Thus, although the instrument used in references 14 and 15 (Agilent 4500) is sensitive, its quadrupole-based mass analyzer may not be well suited to use with multiple labels because, by design, ions of different mass-to-charge ratios pass through sequentially and so data acquisition for multiple labels is slow. Similarly, the instrument used in reference 16 (Thermo Fisher ElementXR and Element2) analyses only one m/Q at a time and have a large settling time for magnet jumps when measuring multiple m/Q values over a range exceeding the range of an electrostatic field jump.

Thus, it is preferred to use a technique which offers substantially simultaneous detection of ions having different m/Q values. For instance, instead of using a point ion detector or single ion detector, it is possible to use an array detector (e.g., see Chapter 29 of ref 17) or a plurality of detectors. Multi-collector sector field ICP-MS instruments can be used (e.g., the Thermo Scientific Neptune Plus, Nu Plasma II, and Nu Plasma 1700 systems), and in particular those having a Mattauch-Herzog geometry (e.g., the SPECTRO MS, which can simultaneously record all elements from lithium to uranium in a single measurement using a semiconductor direct charge detector). These instruments can measure multiple m/Q signals substantially simultaneously. Their sensitivity can be increased by including electron multipliers in the detectors. Sector instruments with an array detector may not be ideal, however, because, although they are useful for detecting relatively high ion signals, they are less useful when signal levels are low, of the level of 1-10 ions per particle event, and so they are not well suited in situations where labels are present at highly variable concentrations. In some embodiments, an array sector or multi-collector may still be utilized. For example, an array detector or multi-collector may be used in embodiments that provide for the deflection of ions to limit detector saturation The most preferred MS method for use with the invention is based on time-of-flight (TOF) detection, which can quasi-simultaneously register multiple masses in a single sample. In theory TOF techniques are not ideally suited to ICP ion sources because of their space charge characteristics, but the inventors have shown that TOF instruments can analyse an ICP ion clouds generated by particles rapidly enough and sensitively enough [18]. Whereas TOF mass analysers are normally unpopular for atomic analysis because of the compromises required to deal with the effects of space charge in the TOF accelerator and flight tube, cytometry methods of the invention can be effective by detecting only the labelling atoms, and so other atoms (e.g, those having an atomic mass below 100) can be removed. This results in a less dense ion beam, enriched in the masses in (for example) the 100-250 Dalton region, which can be manipulated and focused more efficiently, thereby facilitating TOF detection and taking advantage of the high spectral scan rate of TOF. Thus rapid analyses can be achieved by combining TOF detection with choosing labelling atoms that are uncommon in the sample and ideally having masses above the masses seen in an unlabelled sample, e.g., by using the higher mass transition elements. Using a narrower window of label masses thus means that TOF detection to be used for efficient mass cytometry.

Exemplary TOF instruments are available from Tofwerk, GBC Scientific Equipment (e.g., the Optimass 9500 ICP-TOFMS), and Fluidigm Canada (e.g., the CyTOF® and CyTOF®2 instruments). These CyTOF® instruments have greater sensitivity than the Tofwerk and GBC instruments and are known for use in mass cytometry because they can rapidly and sensitively detect ions in the mass range of rare earth metals (particularly in the m/Q range of 100-200 amu) [18]. The instrument settings are already known in the art e.g., reference [18]. Their mass analysers can detect a large number of markers quasi-simultaneously at a high mass-spectrum acquisition frequency on the timescale a single particle transience or of high-frequency laser ablation [16]. They can measure the abundance of labelling atoms with a detection limit of about 100 per cell. Further details on mass cytometry can be found in references 19, 1, 2, and 20.

Labelling of Particles

The invention is suitable for the simultaneous detection of many more than one labelling atom, permitting multiplex label detection e.g., at least 3, 4, 5, 10, 20, 30, 32, 40, 50 or even 100 different labelling atoms. Labelling atoms can also be used in a combinatorial manner to even further increase the number of distinguishable labels. By labelling different targets with different labelling atoms it is possible to determine the presence of multiple targets on a single cell.

Labelling atoms that can be used with the invention include any species that are detectable by ICP-MS and that are substantially absent from the unlabelled sample. Thus, for instance, $^{12}C$ atoms would be unsuitable as labelling atoms because they are naturally abundant, whereas $^{11}C$ could in theory be used because it is an artificial isotope which does not occur naturally. In preferred embodiments, however, the labelling atoms are transition metals, such as the rare earth metals (the 15 lanthanides, plus scandium and yttrium). These 17 elements provide many different isotopes which can be easily distinguished by ICP-MS. A wide variety of these elements are available in the form of enriched isotopes e.g., samarium has 6 stable isotopes, and neodymium has 7 stable isotopes, all of which are available in enriched form. The 15 lanthanide elements provide at least 37 isotopes that have non-redundantly unique masses. Examples of elements that are suitable for use as labelling atoms include Lanthanum (La), Cerium (Ce), Praseodymium (Pr), Neodymium (Nd), Promethium (Pm), Samarium (Sm), Europium (Eu), Gadolinium, (Gd), Terbium (Tb), Dysprosium (Dy), Holmium (Ho), Erbium (Er), Thulium (Tm), Ytterbium (Yb), Lutetium (Lu), Scandium (Sc), and Yttrium (Y). For example, the invention can use any of the isotopes of the lanthanides as listed in the tables in the supplementary information of Reference 4. In addition to rare earth metals, other metal atoms are suitable for detection by ICP-MS e.g., gold (Au), platinum (Pt), iridium (Ir), rhodium (Rh), bismuth (Bi), etc. The use of radioactive isotopes is not preferred as they are less convenient to handle and are unstable e.g., Pm is not a preferred labelling atom among the lanthanides.

In order to facilitate TOF analysis (see above) it is helpful to use labelling atoms with an atomic mass within the range 80-250 amu, e.g., within the range 80-210 amu, or within the range 100-200 amu. This range includes all of the lanthanides, but excludes Sc and Y. The range of 100-200 amu permits a theoretical 101-plex analysis by using different labelling atoms, while permitting the invention to take advantage of the high spectral scan rate of TOF MS. As mentioned above, by choosing labelling atoms whose masses lie in a window above those seen in an unlabelled sample (e.g., within the range of 100-200 amu), TOF detection can be used to provide rapid analyses at biologically significant levels.

Labelling the particles generally requires that the labelling atoms are attached to one member of a specific binding pair (sbp). This labelled member of a sbp is contacted with a sample such that it can interact with the other member of the sbp (the target sbp member) if it is present, thereby localising the labelling atom to a target in the sample. The method of the invention then detects the presence of the labelling atom on a particle as it is analysed by the mass cytometer. Rare earth metals and other labelling atoms can be conjugated to sbp members by known techniques e.g., reference 21 describes the attachment of lanthanide atoms to oligonucleotide probes for ICP-MS detection, reference 22 describes the use of ruthenium to label oligonucleotides, and Fluidigm Canada sells the MaxPar® metal labelling kits which can be used to conjugate over 30 different labelling atoms to proteins (including antibodies).

Various numbers of labelling atoms can be attached to a single sbp member, and greater sensitivity can be achieved when more labelling atoms are attached to any sbp member. For example greater than 10, 20, 30, 40, 50, 60, 70, 80, 90 or 100 labelling atoms can be attached to a sbp member. For example, monodisperse polymers containing multiple monomer units may be used, each containing a chelator such as DTPA. DTPA, for example, binds 3+ lanthanide ions with a dissociation constant of around $10^{-16}$ M [19]. These polymers can terminate in a thiol-reactive group (e.g., maleimide) which can be used for attaching to a sbp member. For example the thiol-reactive group may bind to the Fc region of an antibody. Other functional groups can also be used for conjugation of these polymers e.g., amine-reactive groups such as N-hydroxy succinimide esters, or groups reactive against carboxyls or against an antibody's glycosylation. Any number of polymers may bind to each sbp member. Specific examples of polymers that may be used include straight-chain ("X8") polymers or third-generation dendritic ("DN3") polymers, both available as MaxPar® reagents. Use of metal nanoparticles can also be used to increase the number of atoms in a label.

As mentioned above, labelling atoms are attached to a sbp member, and this labelled sbp member is contacted with the sample where it can find the target sbp member (if present), thereby forming a labelled sbp. The labelled sbp member can comprise any chemical structure that is suitable for attaching to a labelling atom and then for detection according to the invention.

In general terms, methods of the invention can be based on any sbp which is already known for use in determining the presence of target molecules in samples (e.g., as used in IHC or fluorescence in situ hybridisation, FISH) or fluorescence-based flow cytometry, but the sbp member which is contacted with the sample will carry a labelling atom which is detectable by ICP-MS. Thus the invention can readily be implemented by using available flow cytometry reagents, merely by modifying the labels which have previously been used e.g., to modify a FISH probe to carry a label which can be detected by ICP-MS.

The sbp may comprise any of the following: a nucleic acid duplex; an antibody/antigen complex; a receptor/ligand pair; or an aptamer/target pair, a DNA/DNA intercalator pair. Thus a labelling atom can be attached to a nucleic acid probe which is then contacted with a sample so that the probe can hybridise to complementary nucleic acid(s) therein e.g., to form a DNA/DNA duplex, a DNA/RNA duplex, or a RNA/RNA duplex. Similarly, a labelling atom can be attached to an antibody, which is then contacted with a sample so that it can bind to its antigen. A labelling atom can be attached to a ligand, which is then contacted with a sample so that it can bind to its receptor. A labelling atom can be attached to an aptamer ligand, which is then contacted with a sample so that it can bind to its target. Thus labelled sbp members can be used to detect a variety of targets in a sample, including DNA sequences, RNA sequences, proteins, sugars, lipids, or metabolites. A labelling atom can be attached to a molecule which intercalates nucleic acids.

In a typical embodiment of the invention the labelled sbp member is an antibody. Labelling of the antibody can be achieved through conjugation of one or more labelling atom binding molecules to the antibody, for example using the MaxPar® conjugation kit as described above. Antibodies which recognise cellular proteins that are useful for mass cytometry are already widely available for flow cytometry and IHC usage, and by using, for example, polymer or nanoparticle labs which bind multiple atoms of an isotope instead of current labelling techniques (e.g., fluorescence) these known antibodies can be readily adapted for use in methods of the invention, but with the benefit of increasing multiplexing capability. Antibodies used with the invention can recognise targets on the cell surface or targets within a cell. Antibodies can recognise a variety of targets e.g., they can specifically recognise individual proteins, or can recognise multiple related proteins which share common epitopes, or can recognise specific post-translational modifications on proteins (e.g., to distinguish between tyrosine and phosphotyrosine on a protein of interest, to distinguish between lysine and acetyl-lysine, to detect ubiquitination, etc.). After binding to its target, labelling atom(s) conjugated to an antibody can be detected to reveal the presence of that target in a sample.

The labelled sbp member will usually interact directly with a target sbp member in the sample. In some embodiments, however, it is possible for the labelled sbp member to interact with a target sbp member indirectly e.g., a primary antibody may bind to the target sbp member, and a labelled secondary antibody can then bind to the primary antibody, in the manner of a sandwich assay. Usually, however, the invention relies on direct interactions, as this can be achieved more easily and permits higher multiplexing. In both cases, however, a sample is contacted with a sbp member which can bind to a target sbp member in the sample, and at a later stage label attached to the target sbp member is detected.

One feature of the invention is its ability to detect multiple (e.g., 10 or more, and even up to 100 or more) different target sbp members in a sample e.g., to detect multiple different proteins and/or multiple different nucleic acid sequences on particles such as cells or beads. To permit differential detection of these target sbp members their respective sbp members should carry different labelling atoms such that their signals can be distinguished by ICP-MS. For instance, where ten different proteins are being detected, ten different antibodies (each specific for a different target protein) can be used, each of which carries a unique label, such that signals from the different antibodies can be distinguished. In some embodiments, it is desirable to use multiple different antibodies against a single target e.g., which recognise different epitopes on the same protein. Thus a method may use more antibodies than targets due to redundancy of this type. In general, however, the invention will use a plurality of different labelling atoms to detect a plurality of different targets.

If more than one labelled antibody is used with the invention, it is preferable that the antibodies should have similar affinities for their respective antigens, as this helps to ensure that the relationship between the quantity of labelling atoms detected by ICP-MS and the abundance of the target antigen will be more consistent across different sbp's.

If a target sbp member is located intracellularly, it will typically be necessary to permeabilize cell membranes before or during contacting of the sample with the labels. For example when the target is a DNA sequence but the labelled sbp member cannot penetrate the membranes of live cells, the cells of the sample can be fixed and permeabilised. The labelled sbp member can then enter the cell and form a sbp with the target sbp member.

Usually, a method of the invention will detect at least one intracellular target and at least one cell surface target. In some embodiments, however, the invention can be used to detect a plurality of cell surface targets while ignoring intracellular targets. Overall, the choice of targets will be determined by the information which is desired from the method.

General

The term "comprising" encompasses "including" as well as "consisting" e.g., a composition "comprising" X may consist exclusively of X or may include something additional e.g., X+Y.

The term "about" in relation to a numerical value x is optional and means e.g., x±10%.

The word "substantially" does not exclude "completely" e.g., a composition which is "substantially free" from Y may be completely free from Y. Where necessary, the word "substantially" may be omitted from the definition of the invention.

EXAMPLES

Example 1

Characterisation of Narrow Diameter Injector for Use with Particulate Samples

Standard practice in ICP-MS is to nebulise the sample being analysed, and then filter out the large droplets using a spray chamber, such that the particles which are ionised by the plasma are as small as possible. In the analysis of particles, such as cells, by mass cytometry, it is not possible to break the particle down into smaller pieces, because in doing so, it would no longer possible to assign data from the MS to a single particle. In any case, samples with high content of organic matter, such as cells or polystyrene beads, it is customary to use injectors of 2 mm or larger, to prevent clogging of the particle passage to plasma.

Despite this prevailing opinion that large diameter conduits were necessary, the inventors investigated the use of ICP injectors (the conduit that introduces sample into the plasma in the ICP torch) of narrower internal diameter (i.e. less than 2 mm diameter). The standard 2 mm diameter bore injector was compared to injectors of 1.5 mm and 0.85 mm internal diameter. The results of this comparison are set out in FIG. 4A-4D.

In the upper left-hand quarter (FIG. 4A), the results of the different injectors are shown with regard to the CV (coefficient of variance; the extent of variability in relation to mean of the population). The data were determined by running monodisperse particles of known composition (containing Holmium) through the mass cytometer and then analysing the resulting data and the variation in them. This determination therefore indicates that with smaller diameter injectors any differences in results obtained from testing experimental particles can be more conclusively assigned to differences between the particles, not simply apparatus measurement error.

The lower left-hand quarter (4C) shows that when a smaller diameter injector is used, the duration/length of the signal as detected in a TOF-MS for monodispersed particles containing Ho, is lowered (as determined by the number of cycles (pushes) in which the signal peak is detected in the TOF.

Figure 4D:
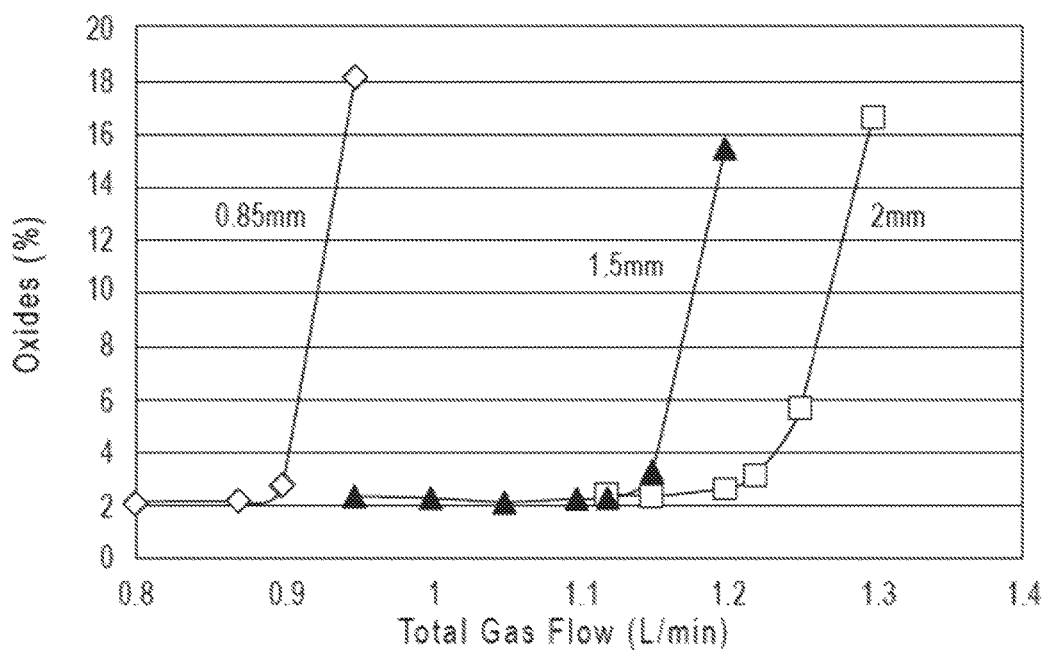

The right hand quarters (4B) show that smaller diameter injectors produce the same quality of data as the standard 2 mm injector. The upper quarter shows that the peak intensity of the signal for all three is approximately 1500 ion counts per particle. FIG. 4D shows how, in order to achieve the same ionization conditions (plasma temperature), which is typically characterized by a ratio of oxide ions to atomic ions, injector gas flow for different injector diameters, is optimized, to get to the same oxide ratio of 2%.

Example 2

Figure 5:
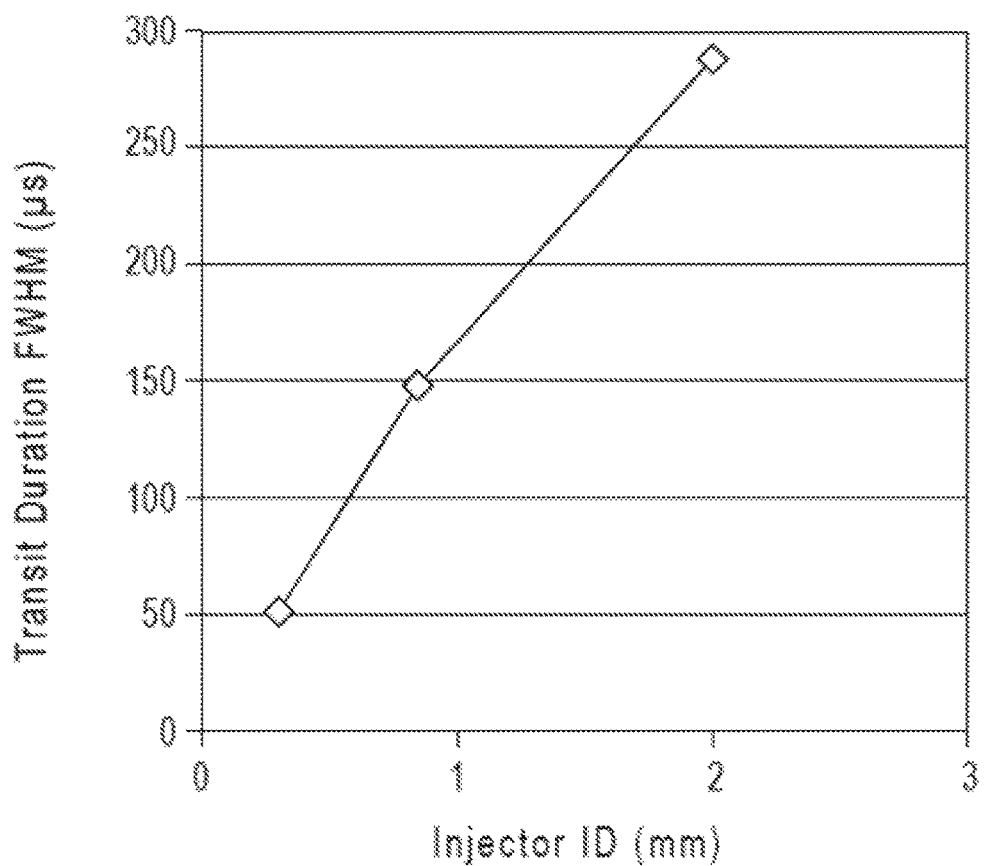
FIG. 5 shows a characterisation of 0.3 mm, 0.85 mm and 1.5 mm ICP torch injectors.

Further Characterisation of Narrow Diameter Injectors for Use with Particulate Samples A second experiment was set up to compare the mean duration of particle-induced transient ion signals for injectors of internal diameters 0.3 mm, 0.85 mm and 1.5 mm. These results are shown in FIG. 5. A 0.2 mm injector was also tested, but was found not to work, because for such a small diameter, the gas velocity is too high for any gas flow, the pressure rises above 15 psi and the flow likely becomes turbulent. The 0.2 mm injector did not provide good data.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

REFERENCES

[1] Tanner et al. (2013) *Cancer. Immunol Immunother.* 62:955-65.
[2] Bodenmiller et al. (2012). *Nat Biotechnol.* 30:858-67.
[3] International Application Publication No. WO2005/093784.
[4] Giesen et al. (2014) *Nature Methods.* 11:417-422.
[5] U.S. Pat. No. 8,536,519.
[6] International Application Publication No. WO2011/098834.
[7] U.S. Pat. No. 8,723,108.
[8] International Application Publication No. WO2014/091243

[9] Stephan et al. (1994) *Vac. Sci. Technol.* 12:405.
[10] Tyler and Peterson (2013). *Surf Interface Anal.* 45:475-478.
[11] Tyler (2014), *Surf Interface Anal.* 46:581-590.
[12] International Application Publication No. WO2006/090138.
[13] U.S. Pat. No. 6,229,142.
[14] Hutchinson et al. (2005) *Anal. Biochem.* 346:225-33.
[15] Seuma et al. (2008) *Proteomics* 8:3775-84.
[16] Giesen et al. (2011) *Anal. Chem.* 83:8177-83.
[17] Herbert and Johnstone, *Mass Spectrometry Basics*, CRC Press 2002.
[18] Bandura et al. (2009) *Anal. Chem.*, 81:6813-22.
[19] Tanner et al. *Cancer Immunol Immunother* (2013) 62:955-965
[20] U.S. Pat. No. 7,479,630.
[21] Brückner et al. (2013) *Anal. Chem.* 86:585-91.
[22] Gao and Yu (2007) *Biosensor Bioelectronics* 22:933-40.

What is claimed is:

1. A method for performing mass cytometry comprising:
providing an elemental standard comprising detectable atoms;
detecting atoms using a mass cytometer comprising an ion source, a mass analyzer, and a detector, wherein detecting atoms comprises detecting the detectable atoms of the elemental standard;
recording a digital signal associated with the detected quantity of detectable atoms as a digital output;
comparing the digital output to an expected digital output, the expected digital output being associated with a measured standard, wherein the measured standard comprises a quantity of the detectable atom; and
modulating a voltage of the detector in response to the comparison of the digital output to the expected digital output so that the digital output associated with the quantity of the detectable atom following modulation of the voltage of the detector returns toward the expected digital output, wherein the expected digital output comprises a ratio of an analog signal associated with the measured standard and a pulse counting signal associated with the measured standard.

2. The method of claim 1, wherein detecting atoms comprises measuring an analog intensity signal and a pulse counting signal associated with the detected quantity of detectable atom and calculating a ratio of the analog intensity signal and a pulse counting signal associated with the detected quantity of detectable atom.

3. The method of claim 1, wherein the voltage of the detector is modulated prior to sample analysis by the mass cytometer.

4. The method of claim 1, wherein the voltage of the detector is modulated during sample analysis by the mass cytometer.

5. The method of claim 1, wherein modulating the voltage of the detector maintains a gain of the detector during or after sample analysis by the mass cytometer.

6. The method of claim 1, further comprising calculating the expected digital output prior to comparing the digital output to the expected digital output and prior to modulating the voltage of the detector by measuring a detector signal produced by a standard and a pulse counting signal associated with the detector signal.

7. The method of claim 6, wherein calculating the expected digital output further comprises determining a ratio of the detector signal produced by the measured standard and the pulse counting signal.

8. The method of claim 1, further comprising calculating the expected digital output prior to comparing the digital output to the expected digital output and prior to modulating the voltage of the detector by measuring a detector signal produced by a known quantity of the detectable atom.

9. The method of claim 1, wherein the expected digital output is associated with an element doped particle.

10. The method of claim 1, wherein the elemental standard comprises:
beads doped with the detectable atoms; or
xenon isotopes, wherein the detectable atoms are the xenon isotopes.

11. A mass cytometer comprising:
an ion source;
an ion detector;
a mass analyser; and
an analog-digital correlator coupled with the ion detector; the analog-digital correlator configured to vary a voltage applied across the ion detector in response to a detector signal associated with an elemental standard, wherein the elemental standard comprises detectable atoms, wherein the analog-digital correlator is configured to vary the voltage applied across the ion detector by comparing the detector signal associated with the elemental standard to an expected digital output, and wherein the expected digital output comprises a ratio of an analog signal associated with the elemental standard and a pulse counting signal associated with the standard.

12. The mass cytometer of claim 11, wherein the analog-digital correlator is configured to vary the voltage of the detector in response to the comparison of the detector signal to the expected digital output so that the digital signal associated with the elemental standard following modulation of the voltage of the detector returns toward the expected digital output.

13. The mass cytometer of claim 11, wherein the analog-digital correlator is configured to vary the voltage of the detector prior to sample analysis by the mass cytometer.

14. The mass cytometer of claim 11, wherein the analog-digital correlator is configured to vary the voltage of the detector during sample analysis by the mass cytometer.

15. The mass cytometer of claim 11, wherein the elemental standard comprises:
beads doped with the detectable atoms; or
xenon isotopes, wherein the detectable atoms are the xenon isotopes.

16. A method for performing mass cytometry comprising:
calibrating a detector of a mass cytometer by:
detecting a quantity of a detectable atom using the mass cytometer comprising an ion source, a mass analyzer, and the detector;
recording a digital signal and an pulse counting signal associated with the detected quantity of detectable atom as an output ratio;
comparing the output ratio to an expected ratio, the expected ratio being associated with a measured standard;
modulating a voltage of the detector in response to the comparison of the output ratio to the expected ratio so that the output ratio associated with the quantity of the detectable atom produced by the detector following modulation of the voltage of the detector returns toward the expected ratio; and
analyzing a sample with the mass cytometer.

17. The method of claim 16, further comprising repeating the calibration of the detector during analysis of the sample with the mass cytometer.

* * * * *